(12) United States Patent
Afzali-Ardakani et al.

(10) Patent No.: US 8,940,148 B2
(45) Date of Patent: Jan. 27, 2015

(54) NANO-FLUIDIC FIELD EFFECTIVE DEVICE TO CONTROL DNA TRANSPORT THROUGH THE SAME

(75) Inventors: Ali Afzali-Ardakani, Ossining, NY (US); Stefan Harrer, New York, NY (US); Binquan Luan, Ossining, NY (US); Glenn J. Martyna, Croton-on-Hudson, NY (US); Dennis M. Newns, Yorktown Heights, NY (US); Hongbo Peng, Yorktown Heights, NY (US); Stanislav Polonsky, Putnam Valley, NY (US); Stephen Rossnagel, Pleasantville, NY (US); Gustavo Stolovitzky, Riverdale, NY (US)

(73) Assignee: International Business Machines Corporation, Armonk, NY (US)

( * ) Notice: Subject to any disclaimer, the term of this patent is extended or adjusted under 35 U.S.C. 154(b) by 63 days.

(21) Appl. No.: 12/820,516

(22) Filed: Jun. 22, 2010

(65) Prior Publication Data
US 2011/0308949 A1    Dec. 22, 2011

(51) Int. Cl.
*B03C 5/02*      (2006.01)
*G01N 33/487*    (2006.01)
(Continued)

(52) U.S. Cl.
CPC .......... *B82Y 15/00* (2013.01); *G01N 33/48721* (2013.01); *B01L 2300/0816* (2013.01);
(Continued)

(58) Field of Classification Search
CPC ...................... G01N 27/447–27/44752; G01N 27/44756–27/453; B03C 5/005–5/028
USPC ................. 204/451, 601, 547, 643, 450, 600; 435/6.1–6.19; 427/58
See application file for complete search history.

(56) References Cited

U.S. PATENT DOCUMENTS 5,795,782 A    8/1998   Church et al.
6,287,832 B1*   9/2001   Becker et al. .............. 435/173.9
(Continued)

FOREIGN PATENT DOCUMENTS

CA     2708782 A1    8/2008
EP     2109685      10/2009
(Continued)

OTHER PUBLICATIONS

Totta, "In-process intergranular corrosion in Al alloy thin films", Journal of Vacuum Science and Technology, vol. 13, Issue: 1, 1976, pp. 26-27.
(Continued)

*Primary Examiner* — Luan Van
*Assistant Examiner* — Maris R Kessel
(74) *Attorney, Agent, or Firm* — Cantor Colburn LLP; Vazken Alexanian

(57) ABSTRACT

The present invention provides a nano-fluidic field effective device. The device includes a channel having a first side and a second side, a first set of electrodes adjacent to the first side, a second set of electrodes adjacent to the second side, a control unit for applying electric potentials to the electrodes and a fluid within the channel containing a charge molecule. The first set of electrodes is disposed such that application of electric potentials produces a spatially varying electric field that confines a charged molecule within a predetermined area of said channel. The second set of electrodes is disposed such that application of electric potentials relative to the electric potentials applied to the first set of electrodes creates an electric field that confines the charged molecule to an area away from the second side of the channel.

10 Claims, 6 Drawing Sheets

(51) Int. Cl.
    B01L 3/00      (2006.01)
    B82Y 15/00     (2011.01)
(52) U.S. Cl.
    CPC ... B01L3/502761 (2013.01); B01L 2400/0421
           (2013.01); B01L 2400/0424 (2013.01); B01L
                   2200/0663 (2013.01); B01L 2300/0896
                   (2013.01); B01L 2300/0645 (2013.01)
    USPC ............................ 204/643; 204/547; 435/6.1

(56) References Cited

U.S. PATENT DOCUMENTS

| | | | |
|---|---|---|---|
| 6,352,838 | B1 | 3/2002 | Krulevitch et al. |
| 6,627,067 | B1 | 9/2003 | Branton et al. |
| 6,685,812 | B2 | 2/2004 | Miles |
| 6,716,620 | B2 | 4/2004 | Bashir et al. |
| 6,905,586 | B2 | 6/2005 | Lee et al. |
| 7,238,485 | B2 | 7/2007 | Akeson et al. |
| 7,279,337 | B2 | 10/2007 | Zhu |
| 7,468,271 | B2 | 12/2008 | Golovchenko et al. |
| 7,625,706 | B2 | 12/2009 | Akeson et al. |
| 2002/0088712 | A1 | 7/2002 | Miles |
| 2003/0085719 | A1 | 5/2003 | Yoon et al. |
| 2004/0011650 | A1 | 1/2004 | Zenhausern et al. |
| 2004/0163955 | A1 | 8/2004 | Miles et al. |
| 2006/0019259 | A1 | 1/2006 | Joyce |
| 2006/0057585 | A1 | 3/2006 | McAllister |
| 2006/0068401 | A1 | 3/2006 | Flory et al. |
| 2009/0038938 | A1 | 2/2009 | Mezic et al. |
| 2009/0093376 | A1 | 4/2009 | Wo et al. |
| 2010/0112667 | A1 | 5/2010 | Sundaram et al. |
| 2011/0224098 | A1* | 9/2011 | Luan et al. ................. 506/16 |
| 2011/0312176 | A1 | 12/2011 | Afzali-Ardakani et al. |

FOREIGN PATENT DOCUMENTS

| | | |
|---|---|---|
| WO | WO-0036407 | 6/2000 |
| WO | WO-0181896 | 11/2001 |
| WO | WO-2006027780 | 3/2006 |
| WO | PCTEP08050562 | 5/2008 |
| WO | WO2008092760 A1 | 8/2008 |
| WO | WO-2008092760 A1 | 8/2008 |
| WO | WO2010044932 A2 | 4/2010 |

OTHER PUBLICATIONS

Schmutz, et al., Corrosion Studies with the Atomic Force Microscope, Part I: Characterization of Potential Inhomogeneities on Passive Surfaces by Surface Potential Imaging, 2005 Vecco Instruments Inc.

Polonsky, et al., "Nanopore in metal-dielectric sandwich for DNA position control," Applied Physics Letters, American Institute of Physics, vol. 91, No. 15, Oct. 18, 2007.

Lin, et al., "Positioning of extended individual DNA molecules on electrodes by non-uniform AC electric fields," Nanotechnology, IOP, vol. 16, No. 11, No. 1, 2005.

D. J. Branton et al., "The potential and challenges of nanopore sequencing," Nature biotechnology, vol. 26, No. 10, 2008, pp. 1146-1153.

K. Jo et al. "A single molecule barcoding system using nanoslits for DNA analysis." PNAS vol. 104, No. 8, 2007, pp. 2673-2678.

D. J. Bonthuis et al., "Conformation and dynamics of DNA confined in slitlike nanofluidic channels," Phys. Rev. Lett., vol. 101, 2008, pp. 108303-108306.

J. J. Kasianowicz et al., "Characterization of Individual Polynucleotide Molecules Using a Membrane Channel," Proc. Natl. Acad. Sci. USA, vol. 93, 1996, pp. 13770-13773.

Z. Zou et al., "Functionalized nano interdigitated electrodes arrays on polymer with integrated microfluidics for direct bio-affinity sensing using impedimetric measurement," Sensors and Actuators A 136, 2007, pp. 518-526.

D. Fologea et al., "Slowing DNA Translocation in a Solid-State Nanopore," American Chemical Society, Nano Letters, 2005, pp. 1734-1737, vol. 5, No. 9.

J. Lagerqvist et al., "Fast DNA Sequencing via Transverse Electronic Transport," American Chemical Society, Nano Letters, 2006, pp. 779-782, vol. 6, No. 4.

J. Li et al., "Ion-Beam Sculpting at Nanometre Length Scales," Macmillan Magazines Ltd., Nature, Jul. 2001, pp. 166-169, vol. 412.

A.J. Storm et al., "Translocation of Double-Strand DNA Through a Silicon Oxide Nanopore," The American Physical Society, Physical Review, 2005, pp. 1-10, E71.

Habib, et al., "Atmospheric oxygen plasma activation of silicon (100) surfaces", Journal of Vacuum Science Technology, May/Jun. 2010.

Kakiuchi, et al., "Highly efficient oxidation of silicon at low temperatures using atmospheric pressure plasma", Appl. Phys. Lett. 90, 091909 (2007).

Han, et al., "Oxygen plasma treatment of gate metal in organic thin-film transistors," Applied Physics Letters, vol. 88, No. 23, pp. 233509-233509-3, Jun. 2006.

Park, et al., "Hybrid silicon evanescent laser fabricated with a silicon waveguide and III-V offset quantum wells", Optics Express, Nov. 14, 2005 / vol. 13, No. 23.

Tizazu, et al., "Photopatterning, Etching, and Derivatization of Self-Assembled Monolayers of Phosphonic Acids on the Native Oxide of Titanium", Langmuir, 2009, 25 (18), pp. 10746-10753.

Tan, et al., "Self-assembled organic thin films on electroplated copper for prevention of corrosion", Journal of Vacuum Science & Technology A: Vaccum, Surfaces, and Films, Jul. 2004, vol. 22, Issue 4, pp. 1917-1925.

Kumiko Ishii et al, Multi-lingual Dynamic KWIC based on Internet Search, IPSJ SIG Technical Report, Nov. 13, 2002, vol. 2002, No. 104, p. 115-121.

Hiroshi Nakagawa, Kiwi: Search System for Multi-lingual Usage Consultation, Journal of JAET, Oct. 1, 2005, No. 6, p. 116-123.

Minoru Yoshida et al, Mining Numbers in Text Using Suffix Arrays and Clustering Based on Dirichlet Process Mixture Models, IPSJ SIG Technical Report, Dec. 15, 2009, H21(4) CD-ROM No. 104, p. 1-8.

Yuya Unno et al, Fast extraction of a compact context set from string search results, The 5th NPL Symposium by IBM Corp, Sep. 2010, p. 1-16, <Search dated on Sep. 2, 2011, URL:http://yans.anlp.jp/symposium/2010/paper/Yans2010_No7.pdf>.

T. Maleki, et al., "A Nanofluidic Channel with Embedded Transverse Nanoelectrodes," Top Publishing Nanotechnology 20 (2009); pp. 1-6.

Notification of Transmittal of the International Search Report and The Written Opinion of the International Searching Authority, or the Declaration; Date of Mailing Aug. 5, 2011; International Application No. PCT/EP2011/059937; Filing Date: Jun. 15, 2011; 6 pages.

H-Y Lin, et al., "Positioning of Extended Individual DNA Molecules on Electrodes by Non-Uniform AC Electric Fields," Institute of Physics Publishing Nanotechnology 16 (2005) pp. 2738-2742.

S. Polonsky, et al., "Nanopore in Metal-Dielectric Sandwich for DNA Position Control," Applied Physics Letter 91, 153103 (2007), American Institute of Physics, Melville, NY US, vol. 91, No. 5, Oct. 8, 2007; pp. 153103-1-153103-3.

Written Opinion of the International Searching Authority, International Application No. PCT/EP2011/059937; International Filing Date: Jun. 15, 2011; 7 pages.

* cited by examiner

NANO-FLUIDIC FIELD EFFECTIVE DEVICE TO CONTROL DNA TRANSPORT THROUGH THE SAME

BACKGROUND OF THE INVENTION

The present invention relates generally to nano-electronics and, more particularly, to a nano-fluidic field effective device and method for controlled transport of a charged molecule.

It is desirable to develop affordable sequencing of the human genome. For example, the sequencing of the human genome can benefit human health care by assisting in the development of personalized medicine. With current fabrication techniques of nano-electronic devices it is possible to design a synthetic nanoscopic device to manipulate, detect and even sequence DNA which may allow for affordable sequencing the human genome.

FIG. 1 shows a top view of an uncovered nano-fluidic device according to the known art in the field. The electrodes 101 and 102 provide a biasing electric field to drive a charged molecule from the cis chamber 103 to the trans chamber 104. The charged molecule is driven through a nanopore 105. Sensors can be built into the nanopore 105 to sense the bases of the DNA as it is driven through the nanopore 105.

The nano-fluidic devices according to the prior art are difficult to fabricate due to the architecture and necessary size of the nanopore. Further, the nano-fluidic devices according to the prior art cannot adequately confine or conform the DNA within the nanopore resulting in impaired sensing of the DNA bases. Therefore, there is a need for an improved nano-fluidic device and method to control the transport of DNA in order to allow for better sensing of DNA bases.

BRIEF SUMMARY OF THE INVENTION

Accordingly, an embodiment of the present invention provides a nano-fluidic field effective device. The device includes a channel having a first side and a second side, a first set of electrodes adjacent to the first side of the channel, and a control unit for applying an electric potential to an electrode. The electrodes of the first set of electrodes are disposed such that application of the electric potential to the first set of electrodes produces a spatially varying electric field that confines a charged molecule within a predetermined area of the channel.

Another embodiment of the present invention provides a method of controlling a charged molecule in a nano-fluidic field effective device. A first electric field is applied in a direction of a flow axis of a channel in the nano-fluidic field effective device to drive the charged molecule therethrough. A second electric field is applied to confine the charged molecule to a predetermined area within the channel.

Another embodiment of the present invention provides a nano-fluidic field effective device. The device includes a channel having a first side and a second side, a first set of electrodes adjacent to the first side of said channel, a second set of electrodes adjacent to the second side of the channel and a control unit for applying an electric potential to an electrode. The electrodes of the first set of electrodes are disposed such that application of the electric potential to the first set of electrodes produces a spatially varying electric field that confines a charged molecule within a predetermined area of said channel. The electrodes of the second set of electrodes are disposed such that application of the electric potential to the second set of electrodes relative to the electric potential applied to the first set of electrodes creates an electric field that confines the charged molecule to an area away from the second side of the channel.

DETAILED DESCRIPTION OF THE INVENTION

In this invention, a charged molecule is driven through a nano- or micro-fluidic channel and electric fields are used to confine the charged molecule, control its conformation and transport it along the channel. The charged molecule can be a long chain polymer such as strands of deoxyribonucleic acid (DNA). By confining, conforming and transporting DNA through a channel a sensing device can be built to allow for relatively affordable and rapid sequencing of DNA.

Figure 2:
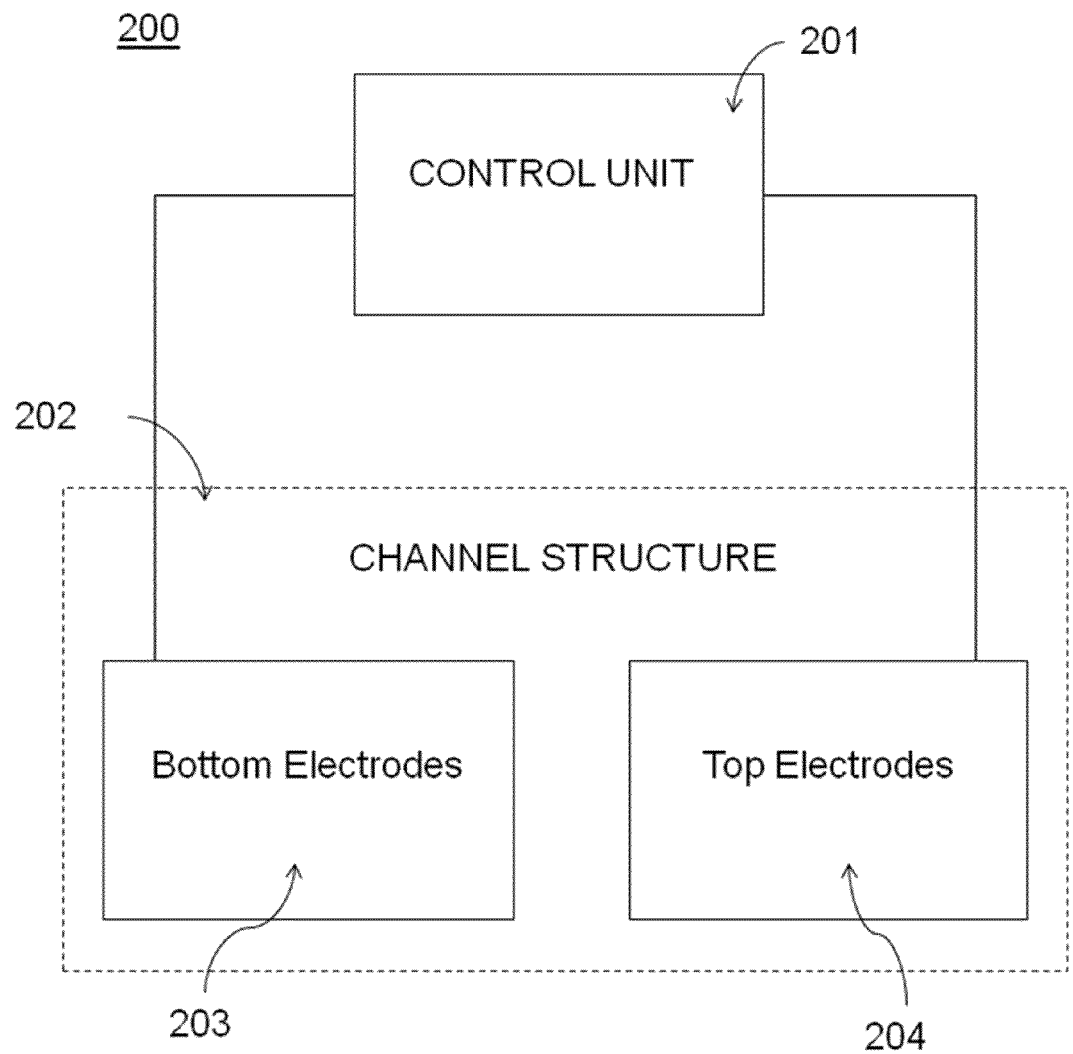
FIG. 2 shows a schematic view of the nano-fluidic field effective device according to an embodiment of the present invention.

FIG. 2 shows a schematic view of the nano-fluidic field effective device 200 according to an embodiment of the present invention. The nano-fluidic field effective device 200 includes a control unit 201 and a channel structure 202 with bottom electrodes 203 and top electrodes 204 disposed within the channel structure. The control unit 201 controls the electric potentials applied to bottom and top electrodes 203, 204 such that electric fields can be produced to drive a charged molecule through the channel structure and to confine the charged molecule within a predetermined area within the channel structure.

Figure 1:
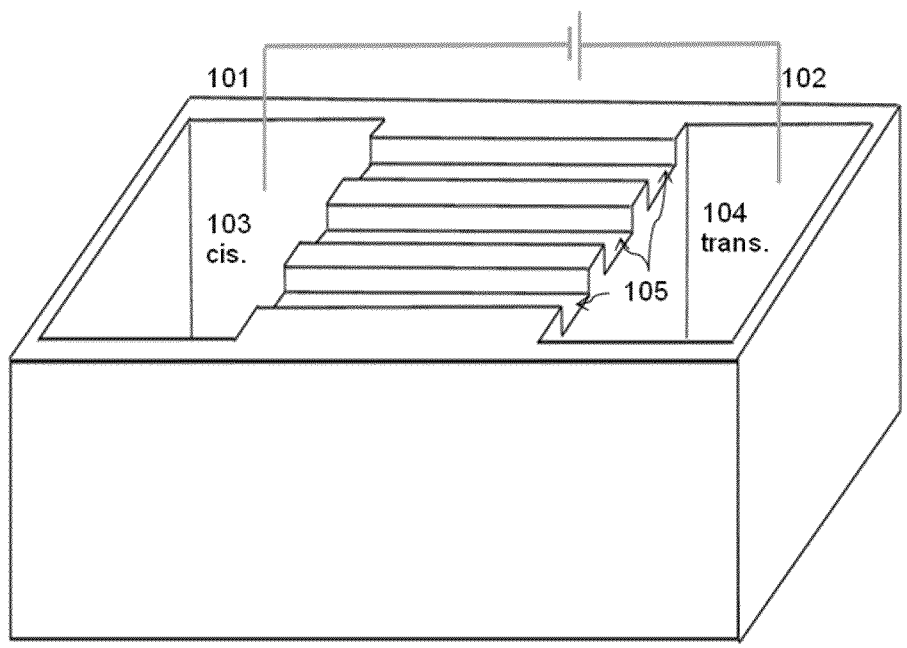
FIG. 1 shows an isometric view of an uncovered nano-fluidic device according to the prior art.
Figure 3:
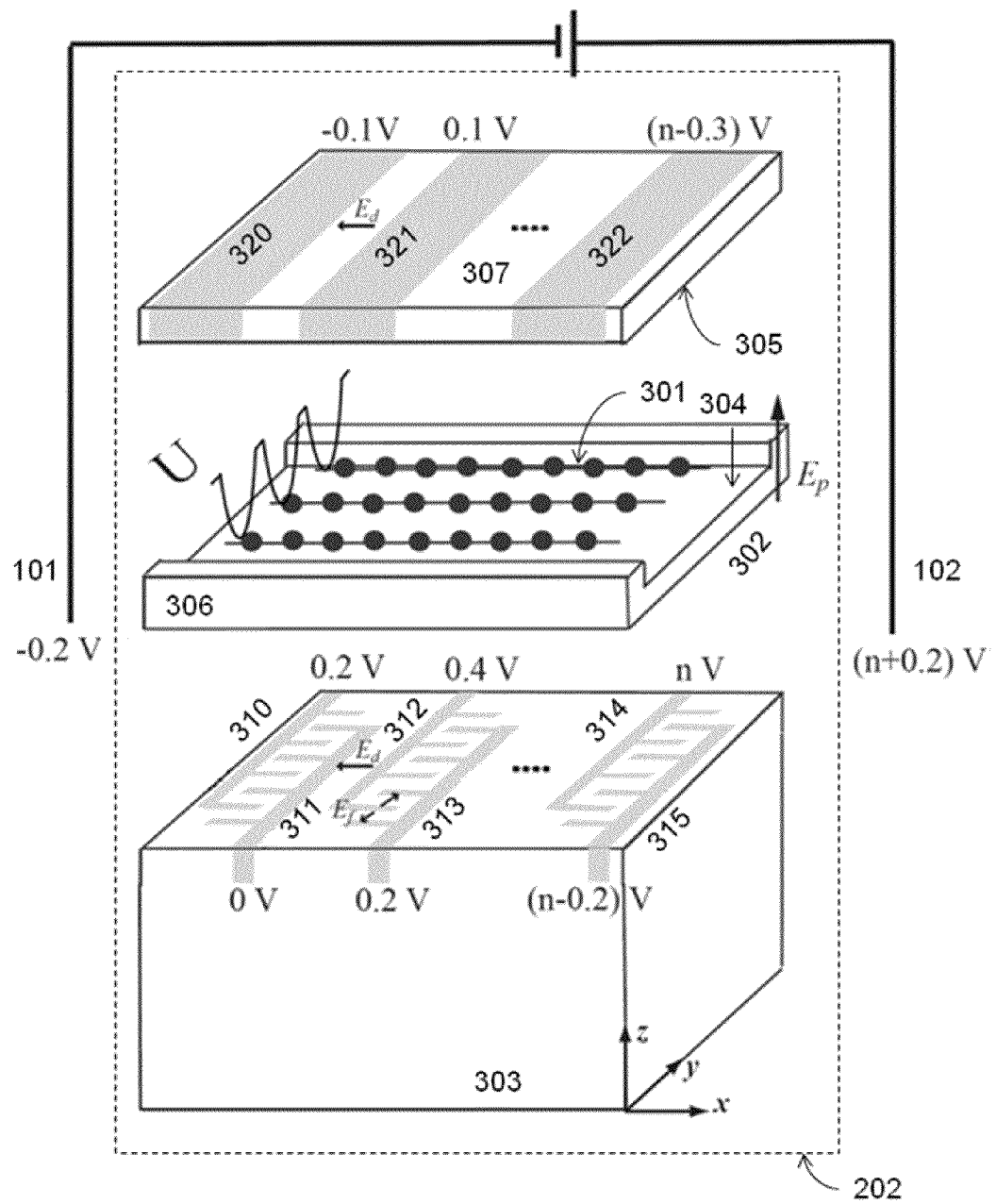
FIG. 3 shows an isometric exploded view of channel structure the nano-fluidic field effective device according to an embodiment of the present invention.

FIG. 3 shows an isometric exploded view of a channel structure 202 of the nano-fluidic field effective device 200 according to an embodiment of the present invention. A cis. chamber electrode 101 and a trans. chamber electrode 102 have electric potentials applied such that an electric field is produced to load charged molecules 301 from a cis. chamber 103 (shown in FIG. 1) into a channel 302 of the channel structure 202. After the charged molecules 301 are driven through the channel 302, the electric field applied by electrodes 101 and 102 pulls the charged molecules 301 out of the channel 302 and into the trans. chamber 104 (shown in FIG. 2).

A first set of electrodes 310-315 is disposed on the surface of a substrate 303 and adjacent to a first side 304 of the channel 302. The electrodes of the first set of electrodes 310-315 are disposed with comb-shaped patterns. By applying electric potentials to a pair of comb-shaped electrodes with interdigitated teeth, such as 310 and 311, a spatially varying focusing field $E_f$ can be created in a y direction, also referred to as a horizontal direction, for confining the charged molecules 301 within a predetermined area, or subslot, of the channel 302. By including multiple teeth on the comb-shaped electrodes with interdigitated teeth 310-315, multiple subslots can be produced such that an equal number of charged molecules 301 can be driven through a single channel 302 as shown. An example of a voltage set-up on the first set of electrodes 301-315 is shown in FIG. 2.

Neighboring electrodes, such as 311 and 312, within the first set of electrodes 310-315 can also provide a biasing electric field $E_d$ to drive the charged molecules 301 in an x direction, also referred to as the flow axis direction. Therefore, the first set of electrodes 310-315 with electric potentials applied can produce electric fields that can constrain and drive charged molecules 301.

When the voltage difference between a pair of comb-shaped electrodes with interdigitated teeth, such as 310 and 311, is 0.2 V, the electric trapping energy U for DNA is $0.2|e|V (l'/l_0) \sim 800 k_B T$, where e is one electron charge, $k_B$ is the Boltzmann constant, T is the temperature, $l_0$ is the spacing between neighboring phosphate groups and l' is the length of each "tooth" in the comb-shaped electrodes (~50 nm). This calculation assumes that the DNA doesn't meander in the trapping potential well, which is satisfied in the trapping potential well generated by narrow "teeth" of comb-shaped electrodes.

In a preferred embodiment, the channel 302 is about 50-nm in depth, 1-um in width and 10-um in length. The size of the channel 302 and sublots can be tailored to the size of the charged molecules 301 used with the device.

The channel 302 has at least a first side 304 and a second side 305, also referred to as a bottom side and a top side, respectively. The bottom side of channel can be the surface of the substrate 303, or as shown, a separate component 306 can form the channel 302. In a preferred embodiment, the bottom side 304 of the channel 302 is coated with a suitable polymer to reduce friction on the charged molecules 301.

In another preferred embodiment, the distance between the first set of electrodes 310-315 and the bottom side 304 of the channel 302 is small, such as, about 3 nm to allow strong focusing $E_f$ and biasing electric fields $E_d$ on the bottom side 304 of the channel 302.

A second set of electrodes 320-322 are disposed on a film 307 and adjacent to a second side 305 of the channel 302. Each of the electrodes in the second set of electrodes 320-322 is opposite a pair of comb-shaped electrodes in the first set of electrodes 310-315. For example, the electrode 320 is opposite the electrodes 310 and 311. Relative to voltages on the first set of electrodes 310-315, voltages on the second set of electrodes 320-322 are applied to produce a vertical electric field $E_p$ to confine or move the charged molecules 301 to an area of the channel 302 away from the second side 305, also referred to a bottom side of the channel 302.

The vertical electric field $E_p$ not only limits the vertical motion of the charged molecules 301 but, in the case of single-strand DNA (ssDNA), also aligns the dipole momentum of each ssDNA base in the z direction, also referred to as the vertical direction. Thus, the resulting ssDNA conformation in three-dimensional electric fields is linear and the ssDNA backbone touches the bottom side of the channel 302 with all bases aligned. This ordered conformation of ssDNA is favorable for allowing a sensor to sense the bases of the DNA.

The nano-fluidic field effective device includes an ionic fluid containing the charged molecules 301. The ion concentration should be chosen so that the Debye length is bigger than the depth of a channel 302, in a preferred embodiment ~50 nm, but is smaller than the spacing between neighboring subslots, in a preferred embodiment ~100 nm. For the preferred embodiment described above, the ion concentration is about 10 micro-molar. This guarantees that electric fields of electrodes in a channel are not screened and interaction between ssDNA molecules are negligible.

In a preferred embodiment, the concentration of charged molecules 301 in the fluid should be equal to or less than 1 per number of subslots in order to avoid two charged molecules 301 entering the same subslot. If the concentration is proper, even if two charged molecules 301 are in the same subslot, because of a strong repulsion between two charged molecules 301 aligned in parallel, the top charged molecule 301 would either diffuse to a neighboring empty subslot or be driven through the channel 302 much faster than the bottom charged molecule 301.

In order to make sure that the head part of a charged molecule 301 in the gap between electrodes, such as the gap between electrodes 311 and 312, does not enter a neighboring subslot, the following relation should be satisfied, $$\Delta R < d, \quad (1)$$

where $\Delta R$ is the deviation from the focus and d is the half spacing between neighboring subslots. Approximately, $$\Delta R = \sqrt{Dt} = \sqrt{D\frac{l}{v}} = \sqrt{D\frac{l}{\mu E}} = \sqrt{\frac{kT}{\xi} \cdot \frac{l}{\mu E}} = l\sqrt{\frac{kT}{q_{eff} V_0}} \quad (2)$$

where D is the diffusion constant; I is the spacing between neighboring electrodes (such as 311 and 312); μ the electrophoretic mobility of the charged molecule; E and $V_0$ are the driving field and voltage difference between neighboring electrodes (such as 311 and 312); respectively; ξ is the friction coefficient and $q_{eff}$ is electrophoretic charge of a charged molecule fragment with a length I. The following relations, $$D = \frac{kT}{\xi}, q_{eff} = \xi\mu \quad (3)$$

were used in above derivation.

Assuming that the charged molecule is DNA, and the spacing between neighboring phosphate groups is $l_0$, $q_{eff}=|e|(l/l_0)$. Since the focusing electric field $E_f$ would drive counterions away from the DNA and the ion concentration is low, the $q_{eff}$ of the DNA can be approximated as the bare charge of DNA. As such, equation (2) can be further rewritten as, $$\Delta R = \sqrt{ll_0} \cdot \sqrt{\frac{kT}{eV_0}} \quad (4)$$

where I=50 nm, $V_0$=0.4 V and $l_0$=0.5 nm, $\Delta R$~1.3 nm<<d. Even l=500 nm, the deviation is still less than d. Therefore the lateral deviation is quite small in DNA's electrophoretic motion.

Figure 4:
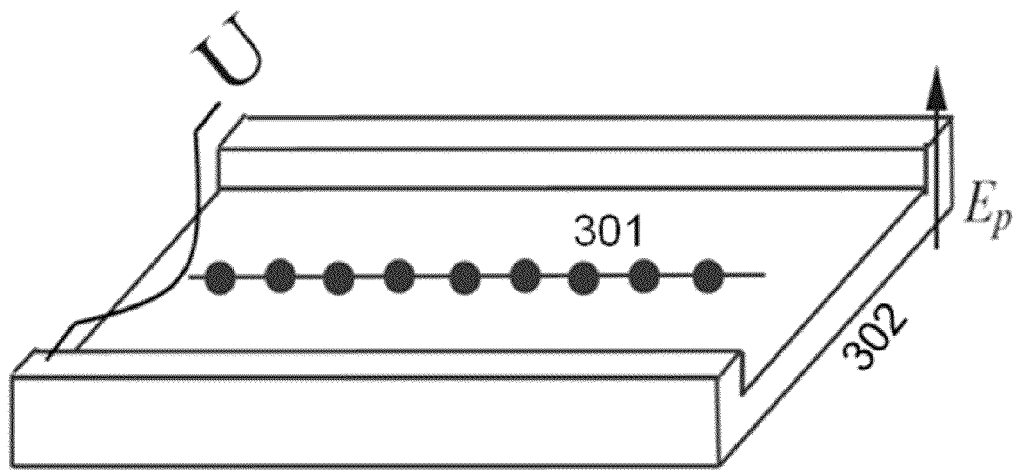
FIG. 4 shows an isometric exploded view of a channel of the nano-fluidic field effective device having a single charged molecule confined therein according to an embodiment of the present invention.

FIG. 4 shows an isometric view of the channel 302 of the nano-fluidic field effective device having a single charged molecule 301 confined therein according to an embodiment of the present invention. If the channel 302 is small, a single subslot within the channel 302 is still beneficial for sequencing DNA. Further, the device is not limited to a single channel 302 but can include multiple channels.

Figure 5:
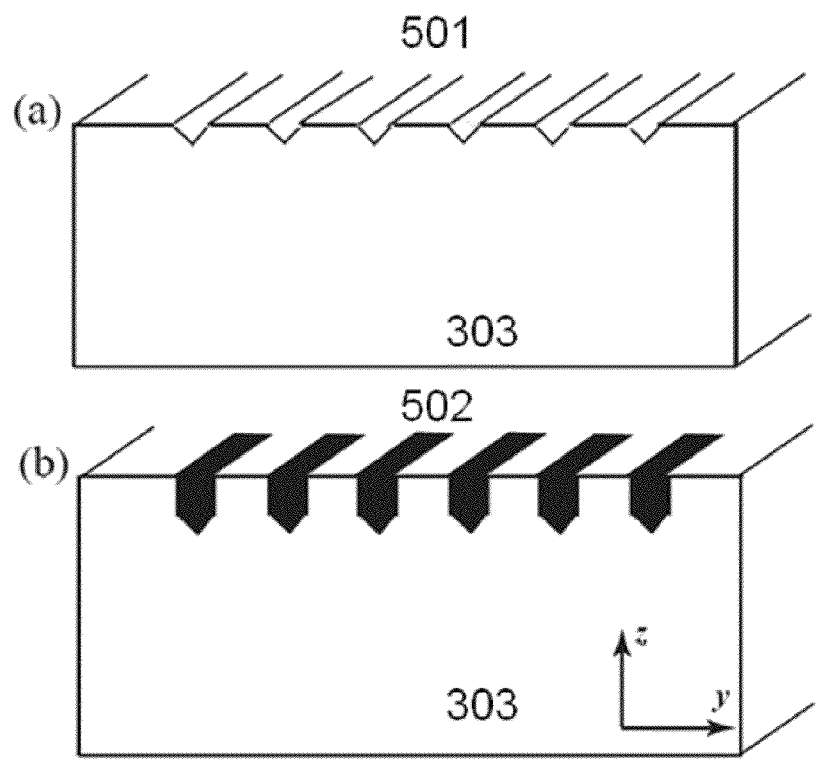
FIG. 5 shows a design of a metal electrode to produce a better focusing electric field according to an embodiment of the present invention.

FIG. 5 shows a design of a metal electrode to produce a better focusing electric field according to an embodiment of the present invention. Limited by the lithography technique, the width of each "tooth" of a comb-shaped electrode (such as 310) can be only about as small as 20 nm. Although electric fields generated from such electrodes are good enough to focus double-strand DNA (dsDNA) (persistence length ~50 nm), it is difficult to apply such electric fields to focus a charged polymer with a much shorter persistence length, such as ssDNA. In order to adequately focus ssDNA the "teeth" of the comb-shaped electrodes must have widths of not more than 3 nm. In preferred embodiment, parallel trenches 501 are etched on the surface of a silica substrate 303. The bottom of a trench 501 can be as small as one atom. Subsequently, metal atoms are deposited inside and above each trench to form "teeth" 502 of the comb-shaped electrodes. This design improves the focusing resolution from 20 nm to about 1 nm. Thus, the focusing electric fields $E_f$ generated by these electrodes can be used to confine ssDNA to a linear conformation.

Figure 6:
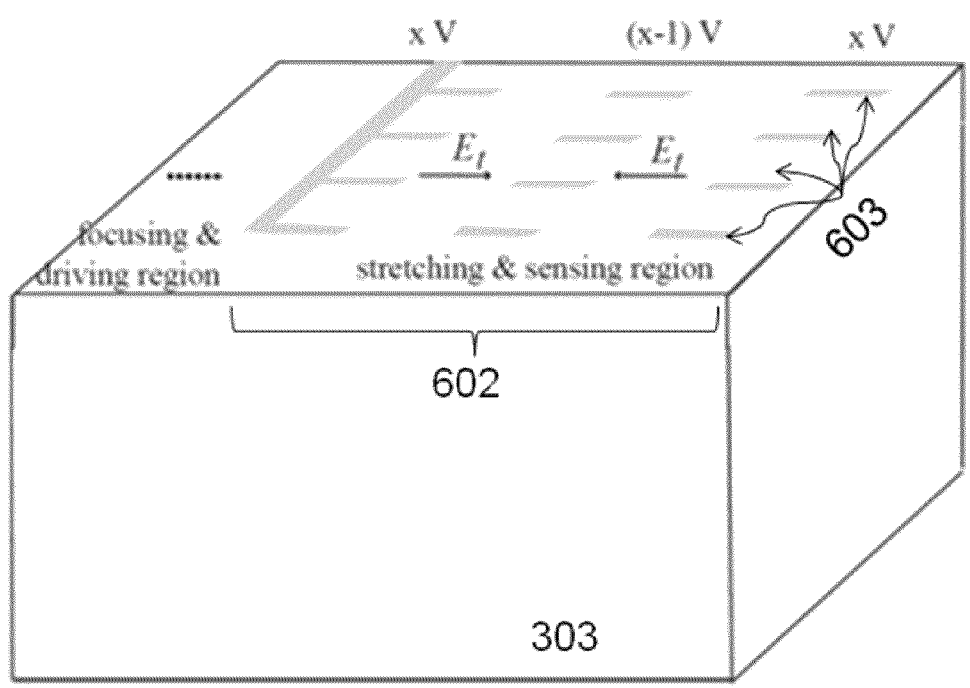
FIG. 6 shows a design of a sensing region for sequencing DNA according to an embodiment of the present invention.

FIG. 6 shows a design of a sensing region for sequencing DNA according to an embodiment of the present invention. In a preferred embodiment of the present invention, electrodes 601 are built on the surface of the substrate 303 and in a region 602 near the exit of the channel such that application of electric potentials creates electric fields for stretching the DNA. The voltage of each of these electrodes is individually controlled, so DNA in each subslot can be stretched individually. In a stretched ssDNA, the spacing between neighboring bases is increased in order to allow for better sensing of DNA bases. Depending on a chosen DNA sequencing technique, a sensor (such as a STM tip) can be built in this region and in each subslot.

Figure 7:
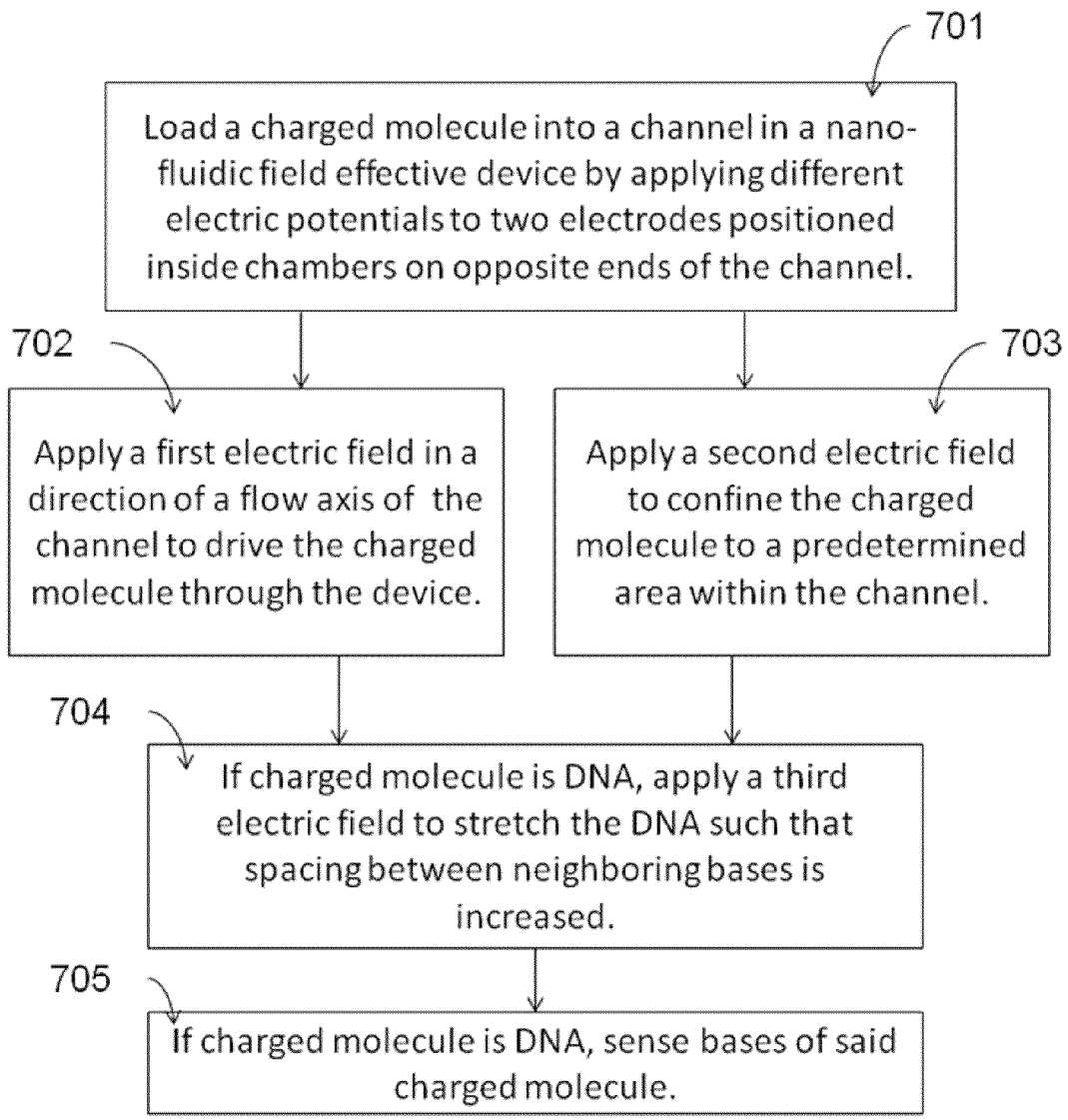
FIG. 7 shows a flow chart for a method of controlling a charged molecule in a nano-fluidic field effective device according to an embodiment of the present invention.

FIG. 7 shows a flow chart for a method of controlling a charged molecule in a nano-fluidic field effective device according to an embodiment of the present invention. In step 701 the charged molecule is loaded into a channel in a nano-fluidic field effective device by applying different electric potentials to two electrodes positioned inside chambers on opposite ends of the channel. In step 702 a first electric field is applied in a direction of a flow axis of a channel in the nano-fluidic field effective device to drive the charged molecule therethrough. In step 703 a second electric field is applied to confine the charged molecule to a predetermined area within the channel. In order to confine the charged molecule the second electric field is spatially varying. If the charged molecule is DNA, in step 704 a third electric field is applied to stretch the DNA such that spacing between neighboring bases in increased. In step 705, the bases of the DNA are sensed in order to sequence the DNA. In all steps, the electric fields can be time-dependent.

The step 702 of applying a first electric field in a direction of a flow axis is carried out by applying electric potentials to neighboring electrodes disposed such that the electric field is applied in the direction of the flow axis.

The step 703 of applying a second electric field to confine the charged molecule to a predetermined area within the channel is carried out by applying electric potentials to electrodes disposed such that the electric field is spatially varying in a horizontal direction. The second electric field can also include an electric field in the vertical direction produced by electrodes disposed on a bottom side and top side of the channel. The electric fields can combine to form a confining electric field within the channel that confines a charged molecule in the vertical and horizontal directions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A nano-fluidic field effective device, comprising:
   a channel having a first side and a second side;
   a first set of electrodes adjacent to said first side of said channel, said first set of Electrodes on a substrate;
   a control unit for applying an electric potential to an electrode; and
   a fluid within said channel containing a charged molecule;
   a spatially varying electric field on said first set of electrodes confining said charged molecule within a predetermined area of said channel, responsive to said electric potential being applied to said first set of electrodes;
   a film comprising a second set of electrodes, said second set of electrodes adjacent to said second side of said channel;
   said film having said second set of electrodes sandwiching said channel between said first set of electrodes on said substrate;
   an electric field on said second set of electrodes confining said charged molecule to an area away from said second side of said channel, responsive to said electric potential being applied to said second set of electrodes;
   said first set of electrodes comprises trenches of metal atoms in said substrate, a bottom of said trenches narrowing to a point;
   wherein said first set of electrodes are pairs of comb-shaped electrodes with interdigitated teeth;
   wherein said second set of electrodes are single electrodes;
   wherein said single electrodes are respectively opposite said pairs of comb-shaped electrodes and are positioned such that one of said single electrodes individually corresponds to a pair of said pairs of comb-shaped electrodes.

2. The nano-fluidic field effective device of claim 1, further comprising a plurality of charged molecules within a plurality of predetermined areas of said channel confined by said first set of electrodes.

3. The nano-fluidic field effective device of claim 1, wherein said teeth of said comb-shaped electrodes have a width not more than 3 nm.

4. The nano-fluidic field effective device of claim 1, wherein said first side and said second side are opposite sides of said channel.

5. The nano-fluidic field effective device of claim 1, wherein at least one of said first side and said second side of said channel has a polymer coating.

6. The nano-fluidic field effective device of claim 1, further comprising:
   a plurality of stretching electrodes located near an exit of said channel.

7. The nano-fluidic field effective device of claim 1, further comprising:
   at least one sensor for sensing bases of said charged molecule.

8. The nano-fluidic field effective device of claim 1, wherein said charged molecule is a long chain polymer.

9. The nano-fluidic field effective device of claim 1, wherein said fluid has an ion concentration such that interaction between charged molecules is negligible.

10. The nano-fluidic field effective device of claim 1, wherein said ion concentration is about 10 micro-molar.

\* \* \* \* \*

UNITED STATES PATENT AND TRADEMARK OFFICE
CERTIFICATE OF CORRECTION

PATENT NO. : 8,940,148 B2
APPLICATION NO. : 12/820516
DATED : January 27, 2015
INVENTOR(S) : Ali Afzali-Azdakani It is certified that error appears in the above-identified patent and that said Letters Patent is hereby corrected as shown below:

On the Title Page

(75) Inventors: Column 1, Line 6, should read as follows:
Ali Afzali-Ardakani, Ossining, NY (US)
Stefan Harrer, New York, NY (US);
Binquan Luan, Ossining, NY (US);
Glenn J. Martyna, Croton-on-Hudson, NY (US);
Dennis M. Newns, Yorktown Heights, NY (US);
Hongbo Peng, Yorktown Heights NY (US);
Stanislav Polonsky, Putnam Valley, NY (US);
Stephen Rossnagel, Pleasentville, NY (US);
Gustavo A. Stolovitzky, Riverdale, NY (US)

Signed and Sealed this
Twenty-sixth Day of April, 2022

Katherine Kelly Vidal
*Director of the United States Patent and Trademark Office*